(12) United States Patent
Thorne et al.

(10) Patent No.: US 8,210,057 B2
(45) Date of Patent: Jul. 3, 2012

(54) MICROFABRICATED TOOLS FOR MANIPULATION OF SMALL SAMPLES

(75) Inventors: Robert E. Thorne, Ithaca, NY (US); Guanhan Chew, Singapore (SG)

(73) Assignee: Cornell University, Ithaca, NY (US)

( * ) Notice: Subject to any disclaimer, the term of this patent is extended or adjusted under 35 U.S.C. 154(b) by 120 days.

(21) Appl. No.: 12/609,379

(22) Filed: Oct. 30, 2009

(65) Prior Publication Data

US 2010/0132483 A1 Jun. 3, 2010

Related U.S. Application Data

(62) Division of application No. 11/698,277, filed on Jan. 26, 2007, now abandoned.

(60) Provisional application No. 60/762,118, filed on Jan. 26, 2006.

(51) Int. Cl.
 *G01N 1/00* (2006.01)
(52) U.S. Cl. ......................................... 73/863
(58) Field of Classification Search ................ None
 See application file for complete search history.

(56) References Cited

U.S. PATENT DOCUMENTS

| | | | | | |
|---|---|---|---|---|---|
| 2,264,489 A | * | 12/1941 | Tiegler et al. | ................ | 248/694 |
| 3,365,761 A | * | 1/1968 | Kalvig | ................ | 248/113 |
| 4,203,180 A | * | 5/1980 | Striplin | ................ | 24/17 B |
| 4,989,820 A | * | 2/1991 | Sterling | ................ | 248/523 |

FOREIGN PATENT DOCUMENTS

WO WO2004/094993 A2 * 11/2004

* cited by examiner

*Primary Examiner* — Hezron E Williams
*Assistant Examiner* — Mark A Shabman
(74) *Attorney, Agent, or Firm* — William Greener; Bond, Schoeneck & King, PLLC (57) ABSTRACT

Microfabricated tools useful for manipulating small, delicate samples are formed from thin plastic films. The films have a small thickness (preferably 5 to 50 micrometers and typically 10 micrometers) and small lateral dimensions (preferably 2 mm or less and typically 0.1 to 1 mm) so that they are reasonably flexible, but are preferably curved by being wrapped around a cylindrical or flat post to give them some rigidity. The softness and thinness of the plastic reduce risk of sample damage during incidental contact with the tool. Its thinness makes it optically and X-ray transparent, so that the samples can be clearly visualized during manipulations and so that the tools can be used to collect X-ray data from samples. As an option, an X-ray sensitive phosphor is incorporated in the film at low concentration. This allows the X-ray beam to be visually located on the mount or tool. The plastic can also be treated to obtain a desired hydrophobicity or hydrophilicity, mechanically embossed or abraded, or coated with films (for example, of polyethylene glycol via pegylation procedures or of PDMS) that promote or inhibit sample adhesion.

3 Claims, 4 Drawing Sheets

MICROFABRICATED TOOLS FOR MANIPULATION OF SMALL SAMPLES

CROSS REFERENCE TO RELATED APPLICATIONS

This application is a Divisional application under 35 U.S.C. 120 of U.S. application Ser. No. 11/698,277, filed Jan. 26, 2007 now abandoned, which claims the benefit under 35 U.S.C. 119(e) of U.S. Application No. 60/762,118, filed Jan. 26, 2006, which is hereby incorporated by reference.

BACKGROUND OF THE INVENTION

1. Field of the Invention

The present invention relates in general to a variety of microfabricated tools that can be employed for manipulating and measuring small (1 mm to 1 micrometer), delicate samples. These samples include macromolecular crystals, small molecule crystals, cells, tissues and cellular organelles. Examples of operations to be performed include measuring sample dimensions and sample temperature, retrieving samples from a solution or growth medium and transferring them from one solution to another, removing samples that are adhered to substrate surfaces, delicately but rigidly gripping and holding the samples, and mounting samples for optical or X-ray examination.

2. Description of the Background Art

Samples such as protein and virus crystals, cells and tissues are extremely fragile and can easily be damaged by incidental contact with hard (e.g., metal) objects. They often adhere to glass slides or glass, plastic or metal containers in which they are grown and are difficult to remove. They often occur together in clusters or encased in other material such as protein skins, gels or lipids, so that they must be separated and extracted in order to study an individual sample. They must often be transferred from one solution or medium to another. Commercial fine-tipped metal tools—such as those in the German-made Micro-Tools™ kits sold by Hampton Research (http://www.hamptonresearch.com/) can be used to accomplish these tasks. However, because of their hardness and stiffness and the inevitable imprecision and vibrations associated with manual movement, they often damage or destroy the samples of interest even with only incidental contact, and they are too large for the smaller samples (100 micrometers or smaller) of increasing interest in, for example, protein crystallography. As a result, a need exists for tools which can be used for handling these small biological samples and other small delicate samples without damaging or destroying the same.

SUMMARY OF THE INVENTION

The present invention fulfills the foregoing need and comprises a number of embodiments of microfabricated tools that are formed from thin plastic films. This fundamental design is derived from the invention disclosed in published US Patent Application No. US 20060086315 (hereinafter, "the '315 application"), which is hereby incorporated by reference in its entirety. The '315 application' discloses a new class of devices for manipulating and mounting crystals for X-ray crystallography and molecular structure determination. These devices consist of a microfabricated polymer film whose base is attached to a cylindrical post. This same basic geometry is used in the present invention to make a variety of tools useful for manipulating and measuring small, delicate samples.

The films have a small thickness (preferably 5 to 50 micrometers and typically 10 micrometers) compared with their lateral dimensions of the order of 1 mm. Consequently, they are reasonably flexible when fabricated using common polymers such as polyimide and mylar. To keep them from flopping from side to side in the presence of fluid and other forces, the films are preferably curved by having their bases wrapped around the post, which gives them some rigidity so that they maintain their shape and orientation relative to the post. In much the same way, leaves and flower petals are made rigid by their curvature, but are so thin and flexible that they will give and bend when, for example, a small force is applied at one end. Alternatively, in applications where flexibility is less important than small size, the rigidity can be obtained by increasing the thickness of the films, and in this case the films can be used without curving around the posts. The softness of the plastic will reduce sample damage compared with metal tools. The thinness of the plastic (relative to the lateral film dimensions) and the resulting small elastic stiffness allows the film to easily bend and give during sample contact, further and dramatically minimizing the chance of sample damage compared with, for example, metal tools. Its thinness makes it optically and X-ray transparent, so that the tools can be used to collect X-ray data from samples attached to them, or to hold samples during examination in an optical microscope. As an option, an X-ray sensitive phosphor such as $CaWO_4$, ZnS:Cu, $CdWO_4$, or $Gd_2O_2S$:Pr is incorporated in the film at low concentration. This allows the X-ray beam to be visually located on the tool. The plastic can also be treated to obtain a desired hydrophobicity or hydrophilicity, or coated with films (for example, of polyethylene glycol via pegylation procedures or of PDMS) that promote or inhibit sample adhesion.

With specific reference to the various embodiments of the present invention, a first embodiment includes tools for sample measurements in which the optical transparency of the polymer film enables the sample being measured to be visualized through the film. The increased rigidity provided by the slight film curvature induced by wrapping the base of the film around the post allows easier measurements in, e.g., viscous liquids. The thinness of the film also allows it to be bent flat if it is pushed down against a flat surface. The softness and flexibility of the tool allow it to be used to push or dislodge from a substrate many soft, delicate, fragile samples like protein crystals, cells, tissues, etc. without damaging them. This softness and flexibility also minimizes the chance of sample damage during incidental contact with the tool. The measuring tool can be placed right next to the sample being measured, for example, within the solution in which it resides, and with its orientation matching the orientation of the sample dimension to be measured. Consequently, the tool can provide accurate measurements under a much wider variety of sample conditions than a microscope reticle, for example, which accurately measures dimensions only of surfaces perpendicular to the optical axis and in the same medium as the outer surface of the lens.

The measuring tools preferably include one or more scales that facilitate measurement of sample dimensions. Measurement of the linear dimensions of sub-millimeter samples, with a resolution of 50 micrometers to 5 micrometers or less, can be obtained. By rotating the scale so that it runs vertically instead of horizontally, the resulting tool can be used to measure the height or thickness above a substrate against which the top edge is placed. Similar orthogonal scales can be patterned on both the top and side edges of a single tool. Orthogonal scales can be patterned around a tool with a square hole, allowing both dimensions of a sample to be measured simultaneously. Instead of patterning scale bars (where there is no film) within a solid area of film, the scale can be formed by regular protrusions from the tool. Microfabrication provides tremendous flexibility in the shape of the measuring device. The markings on the films are produced, for example by photolithographic patterning, that are regularly spaced at standard (e.g., 100 micrometer) intervals either along or perpendicular to the tool axis, allowing measurement of linear dimensions (e.g., width and thickness). The markings can also be regularly spaced in angle, as in a protractor, providing measurements of angular dimensions. Angular markings can also be distributed around an aperture in which the sample to be measured is placed.

Another embodiment of the invention comprises a tool for crystal manipulation, specifically for scooping up delicate samples from solution and allowing the solution to drain away through an open mesh. The mesh size can vary from typically a few micrometers to 100 micrometers or more, depending on the size of samples to be retrieved and the viscosity of the solution in which they reside. These tools can be used to transfer samples to other solutions/media, and to hold samples during soaks in other media. Again, the small thickness and flexibility of these tools allows them to be pushed against the bottom of even very thin (20 micrometer) samples that are adhered to a substrate to gently dislodge them, and then they can slide underneath the sample to scoop it up, with minimal chance of damaging the sample.

A third embodiment of the invention comprises plastic microsaws for cutting soft materials like protein skins, gels, lipid phases, cells and thin tissue layers to extract fragile samples. Protein "skins" (like those which form on milk left at room temperature) are a major obstacle to retrieving crystals from protein crystal growth drops. Crystals are also grown in lipid solutions or gels—soft, porous, water-filled structures—and must be extracted from them. Cell membranes are lipid bilayers. The thickness of protein films is typically a few micrometers, so the pitch of the saw teeth in a saw must be of comparable size for optimal cutting action. The size of the protein drops is typically 1 mm, so cutting tools must be small compared to this size. Microfabrication is thus ideal for producing these small, fine tools. Unlike with metal microsaws, these soft, flexible plastic saws are ideal for cutting soft materials and extracting a sample, and in particular their flexibility minimizes the risk of sample damage due to incidental contact with the blade. Furthermore, since the materials to be cut are very soft, the plastic saws are tough enough to be used many times before becoming dull. Rigidity to the saw blades can be imparted by curving them by wrapping their base around the inside or outside of a round metal or plastic post. Again, the saw blade can be pushed into a substrate so that it bends and lies flat against it, and then can be used to cut away an object that has adhered to the substrate. Because it is so thin it can also be transparent, minimizing visual obstruction of the sample during cutting. If etching or multiple layer deposition is used in fabrication, the thickness of the blade can be tapered near the cutting edge. The film can have a single cutting edge (like a bread knife) or two cutting edges (like a dagger). Tools with a "knife"-like shape without serrations can also be used.

A fourth embodiment of the invention and variations thereon comprise tools for firmly holding fragile samples. The tools of the first three embodiments and those described in the '315 application' all rely either on surface tension/capillary forces between a sample and the tool, on other adhesion forces (such as due to frozen liquid) between the sample and tool, or on gravitational forces to hold the sample to the tool. In many cases, one needs to hold samples more securely. Many sample manipulations—such as plunge cooling in a liquid cryogen, spinning to remove excess liquid, and immersion in a liquid with large surface tension—involve large accelerations and/or large forces that can move and dislodge a sample from a tool. When held in place by, for example, liquid forces, even small external forces like gravity, when allowed to act for a sufficiently long time, can displace the sample relative to the tool. For example, in room-temperature protein crystallography, the crystal tends to slide down the tool (or, in conventional mounting methods using glass capillaries, the capillary wall) during data collection, and this corrupts the X-ray diffraction data. Crystallographers would also like to be able to ship crystals at room temperature to synchrotron X-ray sources, and this requires some way of holding them securely without damaging them during transport and storage for periods of up to a week. More generally, one often wants to rigidly hold a sample during examination, and this is challenging for small, fragile samples like protein crystals and cells.

A number of variations of tools that can be used to securely grip a fragile sample are disclosed herein. Unlike all tools currently used, e.g., in protein crystallography, these tools have a positive capture action that securely grips the sample. In one variation, the tool consists of an aperture lined with a series of small flexible teeth or fingers, and the tool can be pushed down onto a sample to grab it with these fingers. The flexible fingers of the tool deflect upwards as the tool is pushed down onto the sample, eventually grabbing the sample from the sides, similar to washers used in construction to securely grab rods. The width and diameter of these tools is 2 mm or smaller, and the fingers have typical widths of roughly 10-50 micrometers. The combination of the thinness of the plastic film and the small finger width relative to their length produces very soft spring constants that can grab without damaging. The spring constant can be tailored by adjusting the finger width, length and film thickness and the polymer used for the film. The spring constant can be calculated using standard formulas for the stiffness of a beam. The pressure exerted on the sample by each finger can be reduced by flaring the ends of the tips to increase their area of contact with the sample. They can be curved, T-shaped, serrated, etc. to improve gripping action or to tailor their elastic response. If etching is used, the fingers can have different thicknesses, and they can also have various mechanical and chemical surface treatments to increase adhesion to the sample. More generally, microfabrication allows almost unlimited possibilities for the shape and surface properties these tools, including the use of two-layer films in which the fingers of the gripper are made of one material and the rest of the tool is made of a second material. A key feature is that the end of the tool as a whole can elastically bend relative to its base so as to deflect against a surface, as in the previous embodiments, and this facilitates good gripping action. This is especially important when the sample is to be retrieved from a tightly confined space such as a well in a multiple well cell culture or crystallization plate, as the tool's angle of attack may be constrained to be near the vertical direction. The sample can also be pushed down into the tool, using, e.g., one of the tools of the second embodiment.

To improve the grabbing action, a single tool can have "fingers" with a range of lengths, which then grip the crystal at different heights on its side. When the tool is pushed down onto the sample, the longer fingers may deflect upwards, pushing down on the top of the sample, and the shorter fingers may then push up on the bottom of the sample, holding it in place. The shape of the opening can be tailored to match samples of different shapes, such as cubes or rods. For X-ray diffraction applications, the width of plastic around the sample aperture should be minimized while maintaining sufficient width for adequate rigidity. The films can again be curved by wrapping their base around or inside a post to increase their rigidity so that they do not simply flop away when pushed onto the sample. By curving the film in this way, the overall structural rigidity of the tool can be made much greater than that of the fingers.

In another class of tools that have fingers that act in opposition to grab a sample, a central finger or tab is pulled upward or pushed downward (for example, using a rod attached to a manual or robotic micromanipulator). The two "jaws" of the tool can then be positioned around the sample, and then the finger released, to grab the sample. This kind of tool is especially well suited to grabbing thin plates and rods. To improve the grip of the tool, the finger can be patterned with a single, sample-sized hole; the gripping parts of the film can be patterned with holes, serrations or other features; or the film can be coated with a soft or sticky polymer like PDMS. If the tool is made of a transparent polymer, it will minimally obstruct the view of the sample during retrieval. And since the film is flexible and elastic, the lower "jaw" can be pushed into a flat substrate, used to dislodge a sample adhered to it, and then slid under the sample before the jaws are closed. In a two-finger version, the fingers are connected together so that they can be lifted and/or lowered together. In a three-finger version, the three parallel and independent fingers can be deflected independently. For example, the middle finger can be deflected upward and the two outer fingers slid under the sample, and then the middle finger can be released to clamp the sample in place.

Another related class of tools grabs the sample between two flexible paddles. In the simplest case, the film of the tool is flat, and the sample is inserted between the paddles, for example, by pushing the paddles down over the sample, or by lifting one paddle and grabbing the sample between the paddles. The paddles can be fabricated as two separate pieces that are separately attached to a post, or as a single piece, and may have apertures, fingers, serrations or other features to improve the grip on the sample. Compared with "gripper" tools having fingers lining the inside of an aperture, these tools can grip a wider range of sample sizes. They can also effectively grip plate- and rod-like samples, especially if the serrations of opposite paddles are complementary and overlap. Another configuration is to have the two paddles at an angle with respect to each other, produced by wrapping them around a curved post or attaching them to opposite sides of a flat or tapered post. The curvature gives the paddles some stiffness, and a preferential direction of bending when pushed onto a sample. The detailed shape of the paddles can be varied according to the application.

In another embodiment of the present invention, tools are provided that are fabricated flat but pop out into three dimensional structures, as in the Asian art of kirigami. In this embodiment, the flat film pops out to form a three-dimensional basket, which can be used in two ways. First, it can be pushed down onto a sample, causing the basket to be pushed out. The sides of the basket then securely grip the sides of the sample. The plastic must be thin and flexible enough in order for it to remain popped out, and preferably should undergo plastic deformation without breaking.

Another embodiment of the invention comprises tools for sample temperature measurement. In many applications one wants to know the sample's temperature. For example, in cryocrystallography, the sample is placed in a cold gas (nitrogen or helium) stream to keep it cold during X-ray data collection. The sample's temperature varies with how the gas flows are adjusted, with ambient conditions, and with the sample's position in the gas stream. In this embodiment, the sample holders disclosed in the '315 application' as well as any of the tools described here can be formed with an integral thermocouple. The tool is again microfabricated from a polymer like polyimide or mylar. Two different metal layers are patterned and deposited, so that they overlap at the tip, forming a thermocouple junction. The metals may be deposited onto the polymer film by, e.g., sputtering (to reduce heating of the film). Conventional photoresist patterning and wet or dry etching can be used to remove metal to form the final pattern. The extremely small size (10-20 micrometers) of the thermocouple junction, the small cross-sectional area and therefore low thermal conductance of its leads, and the proximity of the junction to sample ensure accurate temperature measurements. The extremely low thermal mass of the junction plus sample holder and the thin film design also ensures a very rapid response in time to changes in temperature. In an alternative design, a thermistor is employed instead of a thermocouple for the temperature sensor. The thermistor can be fabricated by depositing and patterning on the polyimide an amorphous silicon layer. Provided that its lateral dimensions are small, the thermistor can be made quite thin and thus have a small thermal mass, without risk of breakage due to bending.

BRIEF DESCRIPTION OF THE DRAWINGS

The features and advantages of the present invention will become apparent from the following detailed description of a number of preferred embodiments thereof, taken in conjunction with the accompanying drawings, in which:

FIGS. 1A-1D are schematic diagrams of four measurement tool aspects.

FIGS. 4A-4F are illustrations of tools for securely gripping a sample with multiple teeth or fingers.

DETAILED DESCRIPTION OF THE PREFERRED EMBODIMENTS

With reference now to a more detailed consideration of the various preferred embodiments of the present invention, fundamental to each of the microfabricated tool designs is that each is formed from thin film pieces, which are preferably, though not necessarily, wrapped around a cylindrical post. In the tools that use the cylindrical post, horizontal and vertical slits in the lower portion of the films define the positions of the top and sides of the cylindrical post. Preferably, the films are formed from a polymer (plastic), such as polyimide or mylar, which is 5-50 micrometers thick, preferably 10 micrometers, has a very soft spring constant and is less likely to damage fragile samples than, e.g., metal tools. The thinness allows the tip to be easily flattened against a hard substrate, e.g., a glass or plastic surface during measurements. The films have lateral dimensions 1 mm or smaller and are preferably produced by microfabrication methods. In addition, the films are preferably transparent to allow the sample being measured to be visualized through the film. When the tool is to be used in conjunction with a beam of X-rays (or other radiation such as electrons or ultraviolet rays), the film may contain a small concentration of a phosphor sensitive to that radiation (for example, $CaWO_4$ in the case of X-rays.) This allows the X-ray or other illuminating beam to be visually located on the tool. The plastic can also be treated to obtain a desired hydrophobicity or hydrophilicity, mechanically embossed or abraded, or coated with films (for example, of polyethylene glycol via pegylation procedures or of PDMS) that promote or inhibit sample adhesion.

A. Tools for Sample Measurements

Figure 1A:
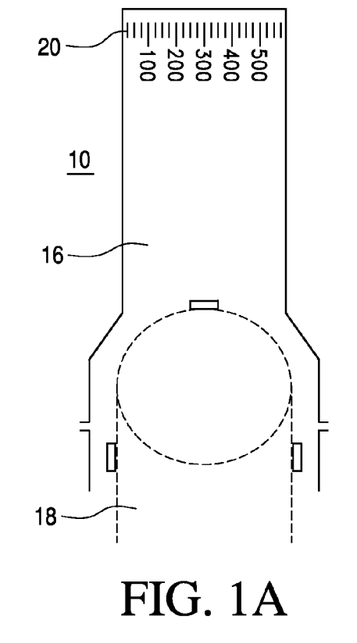
FIG. 1A is a flat top tool with a patterned micrometer scale.
Figure 1B:
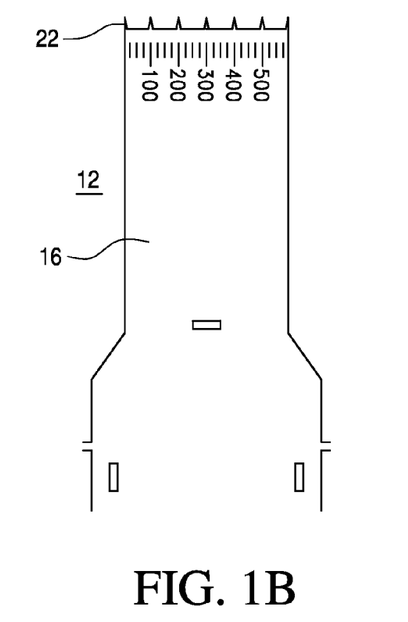
FIG. 1B is a tool with regular protrusions for measuring distances.
Figure 1C:
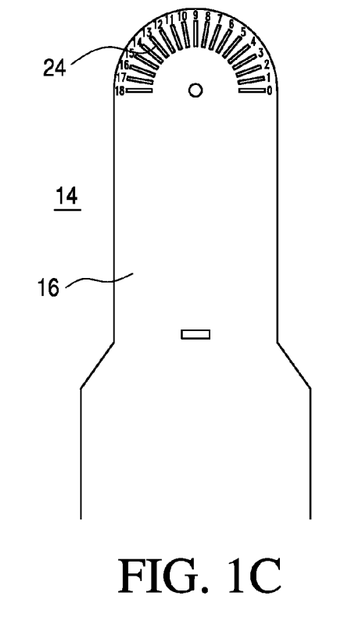
FIG. 1C is a round top tool with a patterned angular scale.

Three variations of the first preferred embodiment of the present invention are illustrated in FIGS. 1A, 1B and 1C, and comprise three kinds of tools 10, 12 and 14, respectively, that can be used for measuring the dimensions of samples, particularly soft, delicate biological samples like protein crystals, cells, tissues, etc. Ideally each tool is made of a transparent polymer film 16, so that the sample being measured can be visualized through it. A slight curvature imparted by attaching the base of the film 16 to a cylindrical, beveled post 18 gives it rigidity, allowing easier measurements in, e.g., viscous liquids. The thinness of the film 16 allows it to be bent flat if it is pushed down against a flat surface. The softness and flexibility of the tool allow it to be used to push or dislodge fragile samples without damaging them. The measuring tool can be placed right next to the sample being measured, e.g., in the solution in which it resides, and with its orientation matching the orientation of the sample dimension to be measured. Consequently, the tools can provide accurate measurements under a much wider variety of sample conditions than a microscope reticle, for example, which accurately measures dimensions only of surfaces perpendicular to the optical axis and in the same medium as the outer surface of the lens.

Figure 1D:
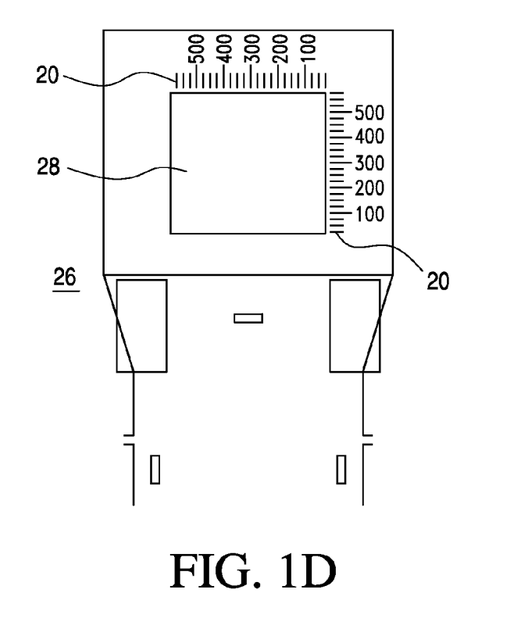
FIG. 1D shows orthogonal scales patterned around a rectangular aperture. The width of the base is roughly 800 micrometers in current designs.

The tool 10 in FIG. 1A includes a scale 20 at the tip end thereof which allows measurement of the linear dimensions of sub-millimeter samples, with a resolution of 50 micrometers to 5 micrometers or less. By rotating the scale 20 so that it runs vertically instead of horizontally, the resulting tool 10 can be used to measure the height or thickness above a substrate against which the top edge is placed. Instead of patterning a scale (where there is no film) within a solid area of film, a scale 22 can be formed by regular protrusions from the tool, as in the tool 12 of FIG. 1B. The tool 14 in FIG. 1C includes a curved scale 24 that allows measurement of angular dimensions of small samples, like a protractor. This is useful for, e.g., measuring the angles between facets of a crystal to determine its crystallographic form. Again, the scale 24 can be formed by regular protrusions on the outer circumference. The tool 26 in FIG. 1D shows how orthogonal scales 20 can be patterned around a rectangular aperture 28, allowing both dimensions of a sample to be measured simultaneously. Similarly, an angular scale can be patterned around a circular aperture. Microfabrication provides tremendous flexibility in the shape of the measuring device.

Preferably, the measurement markings on the films are produced, for example by lithographic patterning, that are regularly spaced at standard (e.g., 100 micrometer) intervals either along or perpendicular to the tool axis, allowing measurement of linear dimensions (e.g., width and thickness). The markings on the film can also be regularly spaced in angle, as in a protractor, providing measurements of angular dimensions.

B. Tools for Crystal Manipulation

Figure 2:
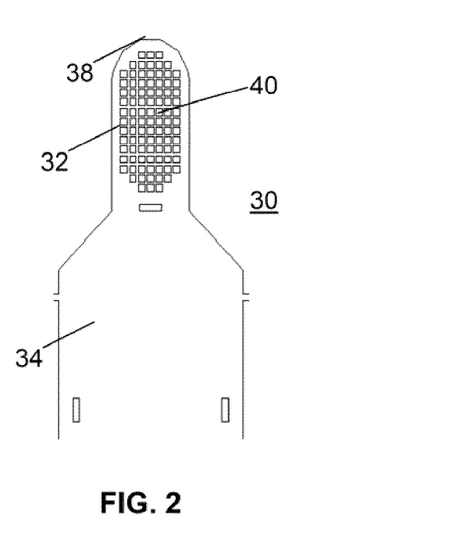
FIG. 2 is an illustration of a mesh tool for sieving out samples from solution, transferring samples between media, and holding them during soaking. The width of the base of the tool is roughly 800 micrometers.

A second preferred embodiment of the present invention comprises tools for manipulating microcrystals and other small, delicate samples. FIG. 2 shows a tool 30 than can be used to sieve out or scoop up delicate samples from solution, allowing the solution to drain away through an open mesh 32. The tool 30 can be used to transfer samples to other solutions/media, and to hold samples during soaks in other media. Note that curvature imparted by wrapping the plastic film 34 around the cylindrical rod (as in 18) is essential to maintaining good rigidity. The thinness of the film allows the tip 38 to be easily flattened against a hard substrate, e.g., a glass or plastic surface, allowing samples adhered to surfaces to be pushed off with minimal chance of damage. Flat, curved or pointed tips are preferably employed for dislodging samples from substrates and for separating samples that have adhered together. The films 34 can have apertures 40 contoured to approximately match the shape of the sample, and with apertures 40 of 30 micrometers to 1 mm, allowing samples to be pulled rather than pushed off substrates to which they have adhered. An array of the apertures 40 forming the mesh 32 can be provided, with aperture sizes from 5 micrometers to 100 micrometers, large enough for excess liquid to flow through but small enough to hold the sample, allowing samples to be scooped up and surrounding liquid removed, or allowing liquid to flow through the mesh 32 to the sample, providing more uniform exposure of the sample to the liquid (important, e.g., in soaking the liquid into a sample).

C. Tools for Cutting Soft Materials to Extract Fragile Samples

Figure 3:
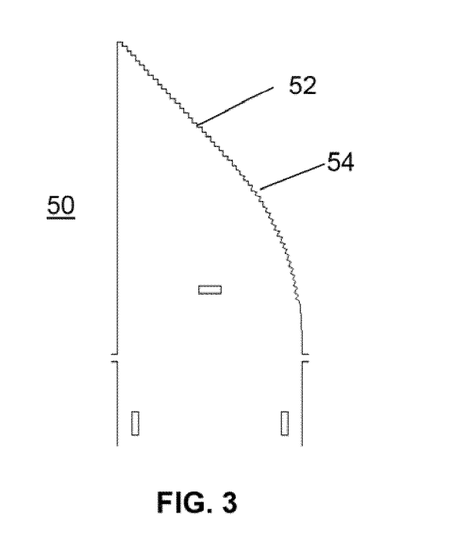
FIG. 3 is an illustration of a flexible plastic saw for cutting soft materials such as protein skins, gels, and gel-like lipid phases. The pitch of the saw teeth is between 5 and 50 micrometers in current designs, suitable for cutting protein skins, and the lateral saw dimensions are roughly 1 mm.

FIG. 3 shows a saw tool 50 designed specifically for cutting soft materials like protein skins, gels, lipid phases, cells and thin tissue layers. Protein "skins" (like those which form on milk left at room temperature) are a major obstacle to retrieving crystals from protein crystal growth drops. Crystals are also grown in lipid solutions or gels—soft, porous, water-filled structures—and must be extracted from them. Cell membranes are lipid bilayers. The thickness of protein skins or films is typically a few micrometers, so the pitch of saw teeth 52 in the saw tool 50 must be of comparable size for optimal cutting action. The size of protein drops used in crystallization and of wells in crystallization and cell culture plates is of the order of 1 mm, so the cutting tool 50 must be comparable to or smaller than this size. Microfabrication is thus ideal for producing these small, fine tools. Unlike with metal microsaws, soft plastic saws are ideal for cutting soft materials and extracting a sample while minimizing risk of sample damage due to incidental contact with the saw blade.

They can also be transparent, allowing the small sample to be viewed more easily during cutting. Furthermore, since the materials to be cut are very soft, the plastic saws are tough enough to be used many times before becoming dull. Rigidity to the saw blades is imparted by curving them, by wrapping them around the inside or outside of a round metal or plastic post. Tools with a "knife"-like shape similar to that in FIG. 3 but without the serrations 52 can also be used. Preferably, a serrated edge 54 with tooth size of 5-50 micrometers, preferably 10-20 micrometers, is employed. The edge can be straight or curved and can be serrated on one or both edges. Alternatively, the saws could also be microfabricated from metal (e.g., tungsten), semiconductor (e.g., silicon nitride) or glass (silicon dioxide) to produce harder saws but that increase the risk of damage to fragile samples D. Tools for Firmly Holding Fragile Samples The tools shown in FIGS. 1-3 and the devices described in the '315 application' all rely either on surface tension/capillary forces between a sample and the tool, on other adhesion forces (such as due to frozen liquid) between the sample and tool, or on gravitational forces to hold the sample to the tool. In many cases, one needs to hold samples more securely. Many sample manipulations—such as plunge cooling in a liquid cryogen, spinning to remove excess liquid, or immersion in a liquid with large surface tension—involve large accelerations and/or large forces that can dislodge a sample from the mount. Even small forces like gravity can cause significant motion over sufficiently long times. For example, in room-temperature protein crystallography, the crystal tends to slide down the tool (or, in conventional mounting methods using glass capillaries, the capillary wall) during data collection, and this corrupts the X-ray diffraction data. Crystallographers would also like to be able to ship crystals at room temperature to synchrotron X-ray sources, and this requires some way of holding them securely without damaging them during transport and storage for periods of up to a week. More generally, one often wants to rigidly hold a sample during examination, and this is challenging for small, fragile samples like protein crystals and cells.

FIGS. 4A-F and 5 show a number of different types of tool that can be used to securely grip a fragile sample. Unlike all tools currently used, e.g., in protein crystallography, these tools have a positive capture action that securely grips the sample.

Figure 4A:
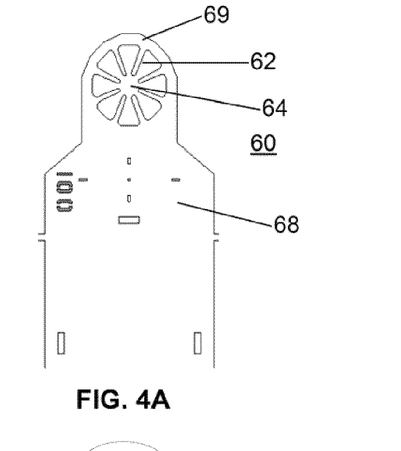
FIG. 4A shows a tool in which small teeth surrounding an aperture grip a sample that is pushed through them.

FIG. 4A shows a tool 60 that can be pushed down onto a sample to grab it with a series of small flexible teeth or fingers 62 that extend inwardly from the edge of an aperture 64. The flexible fingers 62 of the tool 60 deflect upwards as the aperture 64 is pushed down onto the sample, eventually causing the free ends of the fingers 62 to grab the sample from the sides, similar to washers used in construction to securely grab rods. The width and diameter of these tools is approximately 1 mm or smaller, and the fingers 62 have a width of roughly 10-50 micrometers when made using standard plastic films. The combination of the thinness of the plastic film 68 and the small finger width produce very soft spring constants that can grab without damaging. The spring constant can be tailored by adjusting the finger width, length and film thickness. A key feature is that the free end 69 of the tool 60 as a whole can be bent flat against a surface to get good gripping action. The sample can also be pushed down into the tool 60.

Figure 4B:
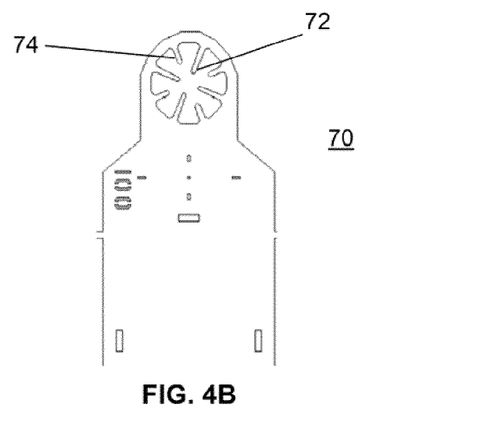
FIG. 4B shows a variation of this tool in which the length of the teeth is varied to produce more secure gripping of samples of different sizes.

To improve the grabbing action, a single tool can have "fingers" with a range of lengths, which then grip the crystal at different heights on its side, as shown in the tool 70 of FIG. 4B. The longer fingers 72 may deflect upwards, pushing down on the top of the sample, and the shorter fingers 74 may then push up on the bottom of the sample, holding it in place.

Figure 4C:
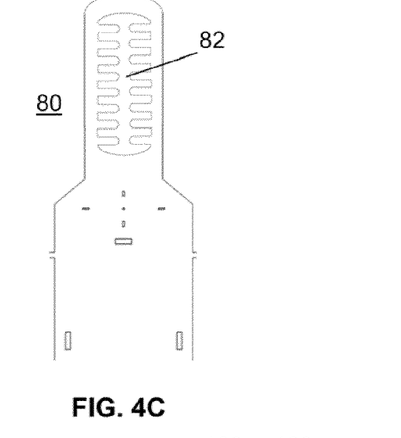
FIG. 4C shows a variation of the tool that is shaped to match the sample shape, in this case an elongated sample.

In the tool 80 of FIG. 4C, the shape of the opening 82 is elongated to match an elongated sample. Thus, the shape of the opening 82 can be tailored to match samples of different shapes, such as cubes or rods, for example.

For X-ray diffraction applications, the width of plastic around the samples should be minimized, consistent with obtaining adequate rigidity. The films can again be curved by wrapping them around or inside a post to increase their rigidity. While the designs shown in FIGS. 4A-4C have narrow teeth, it will be understood that the same basic idea could be implemented with wide teeth.

Figure 4D:
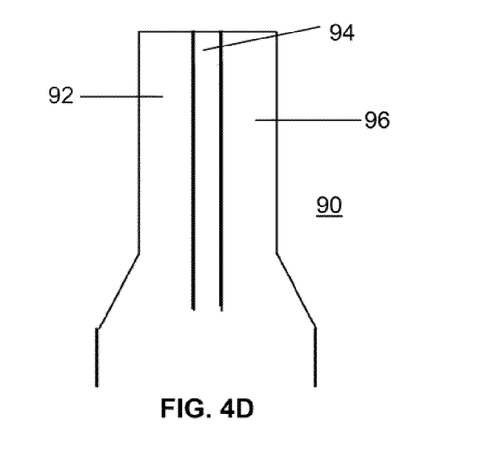
FIG. 4D shows a tool that includes a flat top edge which is slipped under the sample while a central finger is being pulled up.

FIG. 4D shows another tool 90 that has fingers 92, 94 and 96 that act in opposition to grab a sample. In this variation, the central finger 94 is pulled upward (or pushed inward) while the tool is slid under the sample, and then the finger is released, grabbing the sample between the central finger 94 and the outer fingers 92 and 96.

Figure 4E:
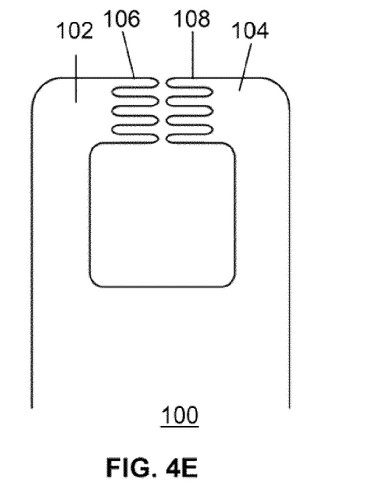
FIG. 4E shows a tool that includes two finger-shaped paddles.
Figure 4F:
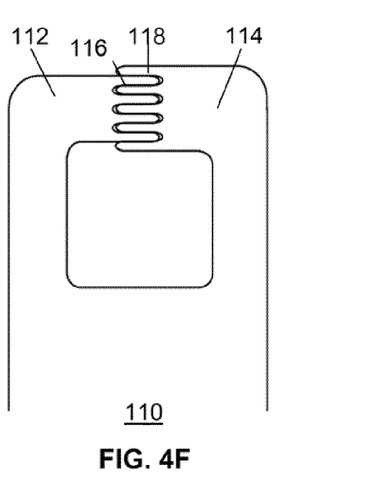
FIG. 4F shows a variation of the tool of FIG. 4E in which the teeth of the paddles are interleaved.

FIGS. 4E and 4F show first and second variations 100 and 110 of a tool in which the sample is inserted between gripping paddles 102 and 104. The detailed shape of the paddles 102 and 104 can be varied according to the application. In the tool 100, the paddles have multiple gripping teeth 106 and 108 that engage the sample. In the tool 110, the teeth 116 and 118 are arranged to be interleaved with one another. The tool designs in FIGS. 4D-4F are especially well suited to gripping rods and plates.

In each of these tools, the sample is actively grabbed and held via a spring-like action in the tool, rather than passively held by adhesion forces or gravity.

E. Tools that are Fabricated Flat but Pop Out Into Three-Dimensional Structures.

Figure 5A:
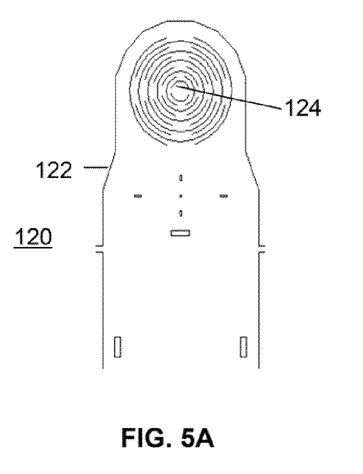
FIGS. 5A and 5B show a microfabricated tool that pops out into a basket and a prototype with the basket popped out, respectively.
Figure 5B:
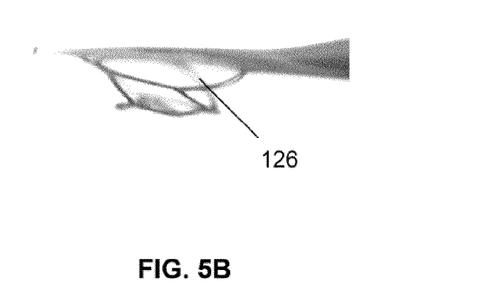

FIGS. 5A and 5B show an example of a general class of tools that are fabricated as a thin film but that pop out into a three-dimensional structure, as in the Asian art of kirigami. In FIG. 5A, the tool 120 consists of a flat film 122 that is cut or etched in a pattern 124 so that it pops out to form a three-dimensional basket type tool 126, as shown in FIG. 5B for an early prototype. The tool 120 can be used in two ways. First, it can be pushed down onto a sample, causing the cut film 124 to be pushed out. The sides of the basket 126 then securely grip the sides of the sample, so that, depending upon sample geometry, these tools can serve the same function as those in FIGS. 4A-4F. Alternatively, the cut film 124 can be popped out by pulling with, e.g., a plastic hook microfabricated by the same process, and then a sample can be scooped up. The plastic must be thin and flexible enough in order for it to remain popped out, and preferably should undergo plastic deformation without breaking.

F. Tools for Sample Temperature Measurement

Figure 6A:
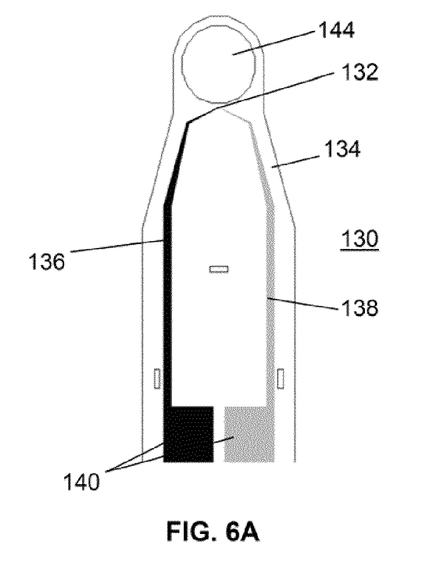
FIGS. 6A and 6B are first and second variations of an embodiment of the present invention for making sample temperature measurements. In the variation of FIG. 6A, a sample holder is combined with a thermocouple, while in FIG. 6B, the sample holder is combined with a thermistor.

In many applications one wants to know the temperature of small samples in the course of making other observations. For example, in cryocrystallography, the sample is placed in cold gas (nitrogen or helium) stream to keep it cold during X-ray data collection. The sample's temperature varies with how the gas flows are adjusted, with ambient conditions, and with its position in the gas stream. FIG. 6A shows a sample mount 130, similar to the ones discussed in the '315 application', but with an integral thermocouple junction 132. The same concept can be applied to any of tools disclosed in the present application, and would be of particular use with the gripping tools 60, 70 and 80.

The mount 130 is again microfabricated from a polymer film 134 like polyimide or mylar. Two different metal layers 136 and 138 are patterned and deposited, so that they overlap at the tip, forming the thermocouple junction 132. The metal layers 136 and 138 may be deposited onto the polymer film 134 by, e.g., sputtering (to reduce heating of the film). Conventional photoresist patterning and wet or dry etching can be used to remove metal to form the final pattern.

In principle just about any metal combination can be used to form the junctions 132, but standard combinations that may be particularly easy to fabricate include type T (copper and copper-nickel) and type J (nickel-chromium and nickel-aluminum.) In the case of type T, the tool could be fabricated using copper-polyimide sheet material used in flexible circuits, in which case only a single metal would need to be deposited. Electrical connections to the thermocouple can be made through the relatively large area pads 140. In the design discussed in the '315 application', these pads 140 can be located below the region of the microfabricated film 134 that is enveloped by the sleeve (e.g., heat-shrinkable tubing) that holds the film to the supporting post 142. Fine thermocouple wire can then be soldered, wire-bonded or otherwise attached to these pads 140. The extremely small size (10-20 micrometers) of the thermocouple junction 132, the small cross-sectional area and therefore low thermal conductance of its leads, and the proximity of the junction 132 to the sample ensure accurate temperature measurements. The extremely low thermal mass of the junction 132 plus sample mount 130 and thin film design also ensures a very rapid temperature response in time. The thermocouple junction 132 can also be formed at the top of the sample aperture 144, with the metals following the periphery of the aperture 144. This has the disadvantage in X-ray crystallography applications of having strongly scattering metal in the path of the X-rays.

Figure 6B:
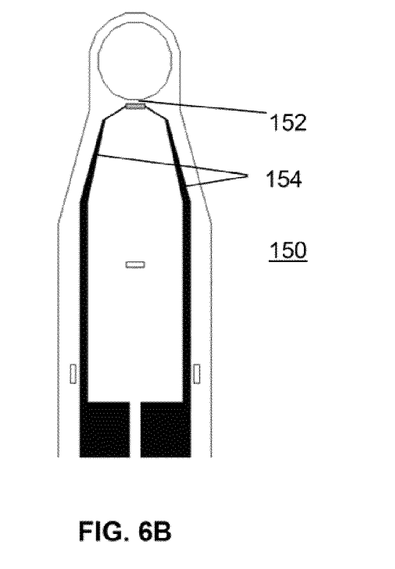

FIG. 6B shows an alternative design of a tool 150 incorporating a thermistor 152 instead of a thermocouple for the temperature sensor. The thermistor 152 can be fabricated by depositing and patterning on the polyimide an amorphous silicon layer. Provided that its lateral dimensions are small, the thermistor 152 can be made quite thin and thus have a small thermal mass, without risk of breakage due to bending. The thermistor is contacted at each end by a single metal 154 such as copper.

Although the invention has been disclosed in terms of a number of preferred embodiments and variations thereon, it will be understood that numerous other variations and modifications could be made thereto without departing from the scope of the invention as defined in the following claims.

We claim:

1. A tool for removeably securing a small, delicate sample, the tool comprising:
    a base member made of thin flexible plastic film and having a base end, a tip end, a first major surface and a second major surface; and
    a plurality of flexible members;
    wherein:
    the tip end comprises an aperture edge defining an aperture in the tip end of the base member;
    the aperture extends from the first major surface to the second major surface;
    the plurality of flexible members are located to extend from the aperture edge into an interior space of the aperture;
    the plurality of flexible members are integrally formed with the thin flexible plastic film that makes up the base member; and
    the plurality of flexible members are structured, located, connected, sized, shaped and/or are sufficiently flexible so that when the small, delicate sample is inserted into the plurality of flexible members the sample will be secured, in a position extending through the aperture, by flexing of the plurality of flexible members from an unflexed position to a flexed position, further wherein the plurality of flexible members are further structured, located, connected, sized, shaped and/or are sufficiently flexible so that the members bend upward as said aperture in said tip end is pushed down over a sample, further wherein each of said members is between 10 and 50 micrometers wide.

2. The tool of claim 1, wherein said members are of at least two different lengths.

3. A tool for removably securing a small, delicate sample, the tool comprising:
    a base member made of thin flexible plastic film and having a base end and a tip end;
    a first arm having a distal end; and
    a second arm having a distal end;
    wherein:
    the first and second arms are located to extend from the vicinity of the tip end to their respective distal ends;
    the first and second arms are integrally formed with the thin flexible plastic film that makes up the base member;
    the distal end of the first arm comprises a plurality of flexible members that extend toward the distal end of the second arm;
    the distal end of the second arm comprises a plurality of flexible members that extend toward the distal end of the first arm; and
    the plurality of flexible members of the first and second arms are structured, located, connected, sized, shaped and/or are sufficiently flexible so that when the small, delicate sample is inserted into the plurality of flexible members the sample will be secured, in a position between the distal ends of the first and second arms, by flexing of the plurality of flexible members from an unflexed position to a flexed position,
    further wherein the plurality of flexible members of the distal end of the first arm are interleaved with the plurality of flexible members of the distal end of the second arm.

* * * * *